(12) United States Patent
Sun et al.

(10) Patent No.: US 6,498,484 B1
(45) Date of Patent: Dec. 24, 2002

(54) METHOD FOR REDUCING RINGING IN NUCLEAR MAGNETIC RESONANCE WELL LOGGING INSTRUMENTS

(75) Inventors: Boqin Sun, Sugar Land, TX (US); Reza Taherian, Stafford, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 88 days.

(21) Appl. No.: 09/594,640

(22) Filed: Jun. 15, 2000

(51) Int. Cl.[7] .................................................. G01V 3/00
(52) U.S. Cl. ........................ 324/303; 324/313; 324/314
(58) Field of Search ................................. 324/303, 314, 324/312, 309, 318, 307, 313

(56) References Cited

U.S. PATENT DOCUMENTS

| | | | |
|---|---|---|---|
| 4,350,955 A | | 9/1982 | Jackson et al. |
| 4,710,713 A | | 12/1987 | Strikman |
| 5,023,551 A | | 6/1991 | Kleinberg et al. |
| 5,055,788 A | | 10/1991 | Kleinberg et al. |
| 5,596,274 A | | 1/1997 | Sezginer |
| 5,712,566 A | | 1/1998 | Taicher et al. |
| 5,796,252 A | * | 8/1998 | Kleinberg et al. ........... 324/303 |
| 6,204,663 B1 | * | 3/2001 | Prammer ..................... 324/303 |

FOREIGN PATENT DOCUMENTS

| | | |
|---|---|---|
| GB | 2311864 A | 10/1997 |
| GB | 2351562 A | 1/2001 |
| WO | WO 98/19175 | 5/1998 |
| WO | WO 98/43064 | 10/1998 |

OTHER PUBLICATIONS

Search Report Under Section 17 dated Feb. 28, 2002 for GB0113140.8.

* cited by examiner

Primary Examiner—Edward Lefkowitz
Assistant Examiner—Tiffany A. Fetzner
(74) Attorney, Agent, or Firm—Kevin P. McEnaney; Brigitte L. Jeffery (57) ABSTRACT

A method for reducing ringing in nuclear magnetic resonance measurements is disclosed. The method includes inducing a static magnetic field in a sensitive volume to orient nuclear magnetic spins of nuclei in the sensitive volume. The nuclear spins are reoriented by a first selected angle. An amplitude of the static magnetic field is then adjusted to cause a first selected phase shift in a spin echo signal measured subsequently to the reorienting by the first angle. The spins are then reoriented by a second selected angle, and a first spin echo signal is detected. After a selected wait time, reorienting by the first selected angle is repeated. Adjusting the amplitude of the static magnetic field is then repeated to cause a second selected phase shift in a subsequently measured spin echo. The first and second selected phase shifts have a difference between them of an odd numbered multiple of 180 degrees. Reorienting by the second selected and detecting a second spin echo signal are then repeated. Finally, a difference between the first spin echo signal and the second spin echo signal is determined. In one embodiment, the measuring of the first and second spin echoes is repeated a selected number of times, and the difference is calculated between time corresponding ones of the first and second spin echoes.

20 Claims, 6 Drawing Sheets

METHOD FOR REDUCING RINGING IN NUCLEAR MAGNETIC RESONANCE WELL LOGGING INSTRUMENTS

FIELD OF THE INVENTION

The invention is related generally to nuclear magnetic resonance apparatus and methods. More specifically, the invention is related to methods and apparatus for reducing ringing in nuclear magnetic resonance instruments.

DESCRIPTION OF THE RELATED ART

Nuclear magnetic resonance (NMR) instruments have been adapted for use in wellbores drilled through earth formations. Generally speaking, NMR instruments used for analyzing earth formations include a magnet for inducing a static magnetic field in the earth formations to be evaluated, an antenna placed proximate to the formations to be analyzed, and circuitry adapted to conduct radio-frequency (RF) power pulses through the antenna to induce an RF magnetic fields in the same formations. The circuitry also includes a receiver adapted to detect signals induced in the antenna (or a separate receiving antenna). The induced signals are related to NMR phenomena induced in the formation of interest; by the combined action of the static magnetic field and the RF magnetic field.

Typically, measurement of NMR related phenomena in the earth formation is performed by allowing some time for the static magnetic field to polarize nuclei in the formation in a direction substantially along the direction of the static magnetic field. A first one of the RF pulses passed through the antenna has a magnitude and duration selected to reorient the nuclear magnetization by about 90 degrees from its previous orientation. After a selected time, successive RF pulses are passed through the antenna, each of these having a magnitude and duration selected to reorient the nuclear spin axes by about 180 degrees for their immediately previous orientations to enable the nuclear spin axes to "rephase" or realign with each other. The induced signals, known as "spin echoes", are generally measured during the time interval between each successive one of the "180 degree" RF pulses. The succession of spin echo measurements is generally known as a "sequence". The amplitude of the spin echo signals, and the rate at which the spin echo amplitudes change during a measurement sequence, are related to properties of interest of the earth formations, such as fractional volume of pore space (porosity) and the properties of fluids present in the pore spaces. The frequency of the RF magnetic field needed to reorient the nuclear magnetization, which is the frequency of the spin echo signals, is related to the amplitude of the static magnetic field and a factor, known as the gyromagnetic ratio γ, which is unique to each isotope. For evaluation of earth formations, the static magnetic field amplitude and RF magnetic field frequency are typically selected to excite NMR phenomena in hydrogen nuclei, although other nuclei may be used for NMR evaluation of earth formations.

Exciting the antenna with RF power pulses in the presence of a strong static magnetic field causes mechanical excitation of the antenna. Mechanical excitation of the antenna leads to excitation of a signal, called "ringing", in the antenna. The ringing is unrelated to NMR phenomena, and frequently has a very large amplitude. The amplitude of the ringing is often highest right after application of each RF pulse, and is of such a magnitude as to make it difficult to measure the amplitude of NMR induced signals. Reducing the effects of ringing on NMR measurement is very important in well logging applications, among others, because significant information about the properties of the earth formations are determined by the amplitudes of spin echoes occurring shortly after the RF pulses.

Several methods are known in the art for reducing ringing. One class of such methods includes creating a phase difference between the ringing signal and the NMR induced signals, and summing or "stacking" multiple sets of measurements to reduce the amplitude of the ringing signal in the output. One commonly used measurement sequence used in evaluation of earth formations is known as "phase alternate pairs" (PAPS). PAPS sequences include performing a measurement sequence as just described including a 90 degree RF pulse followed by successive 180 degree pulses. After a selected wait time, another such measurement sequence is performed, but with the polarity of the 90 degree pulse reversed. Stacking the two sets of measurements substantially cancels the ringing signal. Such a method is described, for example, in U.S. Pat. No. 5,596,274 issued to Sezginer and U.S. Pat. No. 5,023,551 issued to Kleinberg et al.

Another device for reducing ringing is to have the magnet arranged so as to dispose the antenna in a region having substantially zero static magnetic field amplitude. A NMR apparatus which has this arrangement is described, for example, in U.S. Pat No. 5,712,566 issued to Taicher.

Yet another device for reducing ringing is to provide separate antennas for inducing the RF magnetic field and detecting the NMR induced signals, where these two antennas are substantially orthogonal to each other. Ringing induced in the transmitting antenna is substantially undetected by the receiving antenna. See for example, the Taicher et al '566 patent referred to previously.

Still another device known in the art for reducing ringing is to select more than one RF frequency for exciting NMR phenomena and stacking the signals at the multiple frequencies to reduce the amplitude of the ringing. See for example International Patent Application No. WO 98/43064 filed by Prammer.

Still another method for reducing ringing is disclosed in U.S. pat. app. Ser. No. 09/102,719 filed Jun. 22, 1998 entitled *Method for Eliminating Ringing During a Nuclear Magnetic Resonance Measurement,* and assigned to the same assignee as this invention. The method described in the application includes measuring an NMR sequence including ringing and NMR signal, canceling the NMR signal from a part of the sequence to determine the ringing signal, measuring signal from a second part of the sequence which is substantially without NMR signal, and using the ringing thus determined in the second part of the sequence to correct the signal (ringing plus NMR signal) measured during the first part of the sequence for the effects of ringing and other spurious noise.

Still another method for reducing the effects of ringing on NMR signal detection is described in U.S. pat. app. Ser. No. 09/276,049 filed Mar. 25, 1999 entitled *Nuclear Magnetic Resonance Well Logging Method and Apparatus,* and assigned to the assignee of this invention. The method described in this application includes, practically speaking, measuring two sets of PAPS measurement sequences wherein the second PAPS sequence set induced in a manner such that the NMR signal (spin echo) polarity is reversed with respect to the first set. Subtracting time-corresponding signals in the second PAPS set from those in the first PAPS set effectively cancels the ringing signal attributable to the 90 degree pulse.

SUMMARY OF THE INVENTION

The invention is a method for reducing ringing in nuclear magnetic resonance measurements. The method includes inducing a static magnetic field in a sensitive volume to orient nuclear magnetic spins of nuclei in the sensitive volume. The nuclear spins are reoriented by a first selected angle. Typically this is performed by applying an oscillating magnetic field to the sensitive volume having an amplitude and duration selected to reorient the spins by the first selected angle. An amplitude of the static magnetic field is then adjusted to cause a first selected phase shift in a spin echo signal measured subsequently to the reorienting by the first angle. The spins are then reoriented by a second selected angle, and a first spin echo signal is detected. The reorienting by the second selected angle is also typically performed by applying an oscillating magnetic field to the sensitive volume, having a duration and amplitude selected to cause reorienting by the second selected angle. Exemplary values for the first and second selected, angles are 90 and 180 degrees, respectively. The oscillating magnetic field frequency is typically selected to be the nuclear magnetic resonance frequency of the nuclei of interest in the sensitive volume.

After a selected wait time, reorienting by the first selected angle is repeated. Adjusting the amplitude of the static magnetic field is then repeated to cause a second selected phase shift in a subsequently measured spin echo. The first and second selected phase shifts have a difference between them of an odd numbered multiple of 180 degrees. Reorienting by the second selected and detecting a second spin echo signal are then repeated. Finally, a difference between the first spin echo signal and the second spin echo signal is determined.

In one embodiment, the measuring of the first and second spin echoes is repeated a selected, number of times, and the difference is calculated between time corresponding ones of the first and second spin echoes.

In one embodiment, the first and second selected phase shifts are 180 and 0 degrees, respectively. In another embodiment, the first and second selected phase shifts are +90 and −90 degrees respectively.

DETAILED DESCRIPTION

Figure 1:
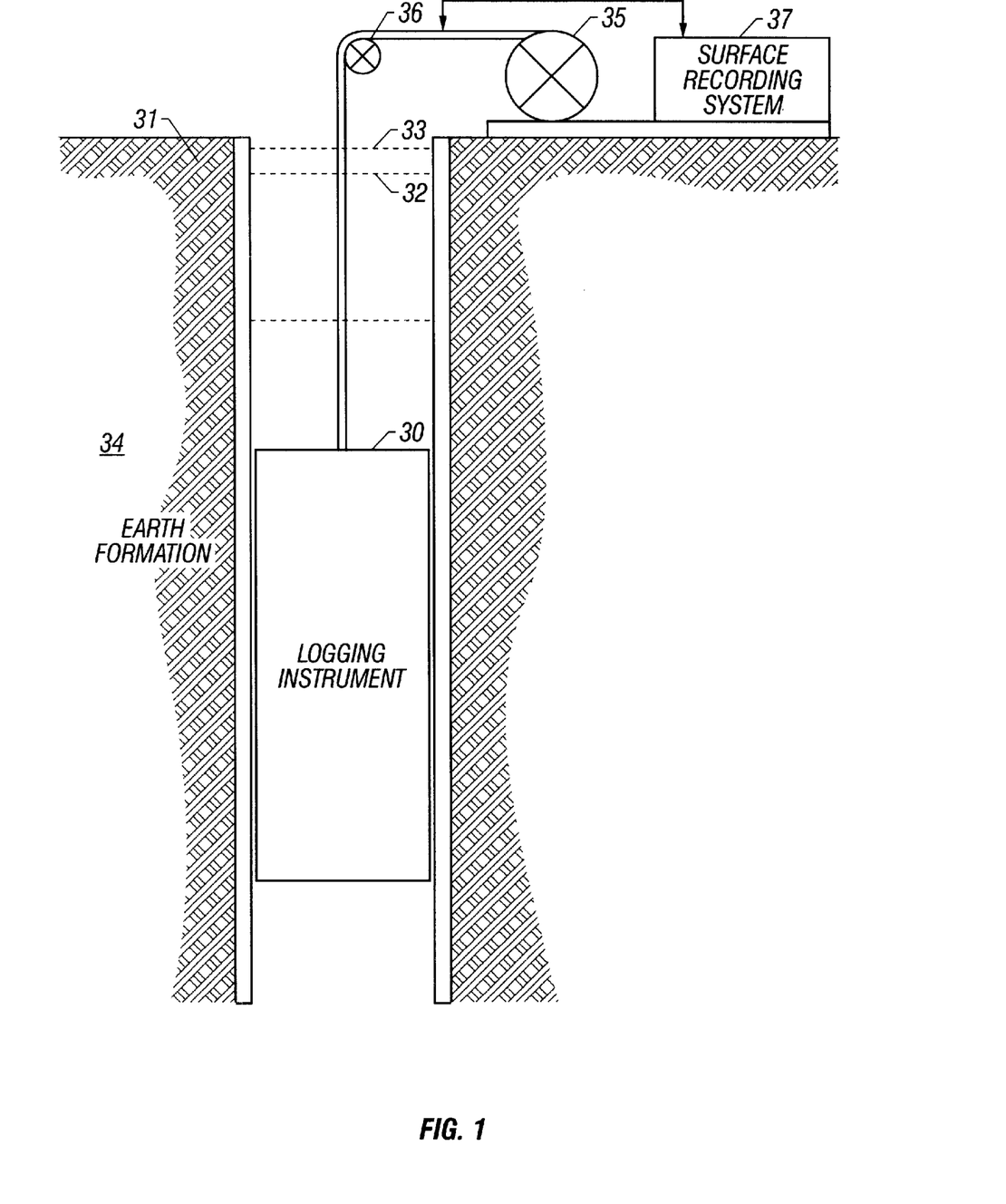
FIG. 1 shows a general view of a well logging instrument disposed in a wellbore drilled through earth formations.

FIG. 1 shows in general form, an example well logging instrument which can be used with the invention. The logging instrument 30 is typically attached to one end of an electrical cable 33 to be lowered into and retrieved from a wellbore 32 drilled through earth formations shown generally at 31 and 34. The cable 33 is extended and retracted by a winch 35 or similar device known in the art. Electrical power is sent to the instrument 30, and signals are returned from the instrument 30 for recording and interpretation in a surface recording system 37. Typically a record of the signals transmitted by the instrument 30 is made in the surface recording system 37, with respect to depth in the wellbore 31 by using signals from a cable length measuring encoder 36 of any type well known in the art. As is well known in the art, measurements made by the instrument 30 may also be made with respect to time, and a record of the measurements with respect to depth can be generated later by correlation with a record of instrument depth with respect to time which can be recorded in the surface recording system 37 during measuring operations.

The instrument 30 can be any type known in the art suitable for making nuclear magnetic resonance (NMR) measurements in the wellbore. Such instruments are described, for example, in U. S. Pat. No. 5,055,788 issued to Kleinberg et al, U.S. Pat. No. 5,712,566 issued to Taicher et al and U.S. Pat. No. 4,350,955 issued to Jackson et al.

Figure 2:
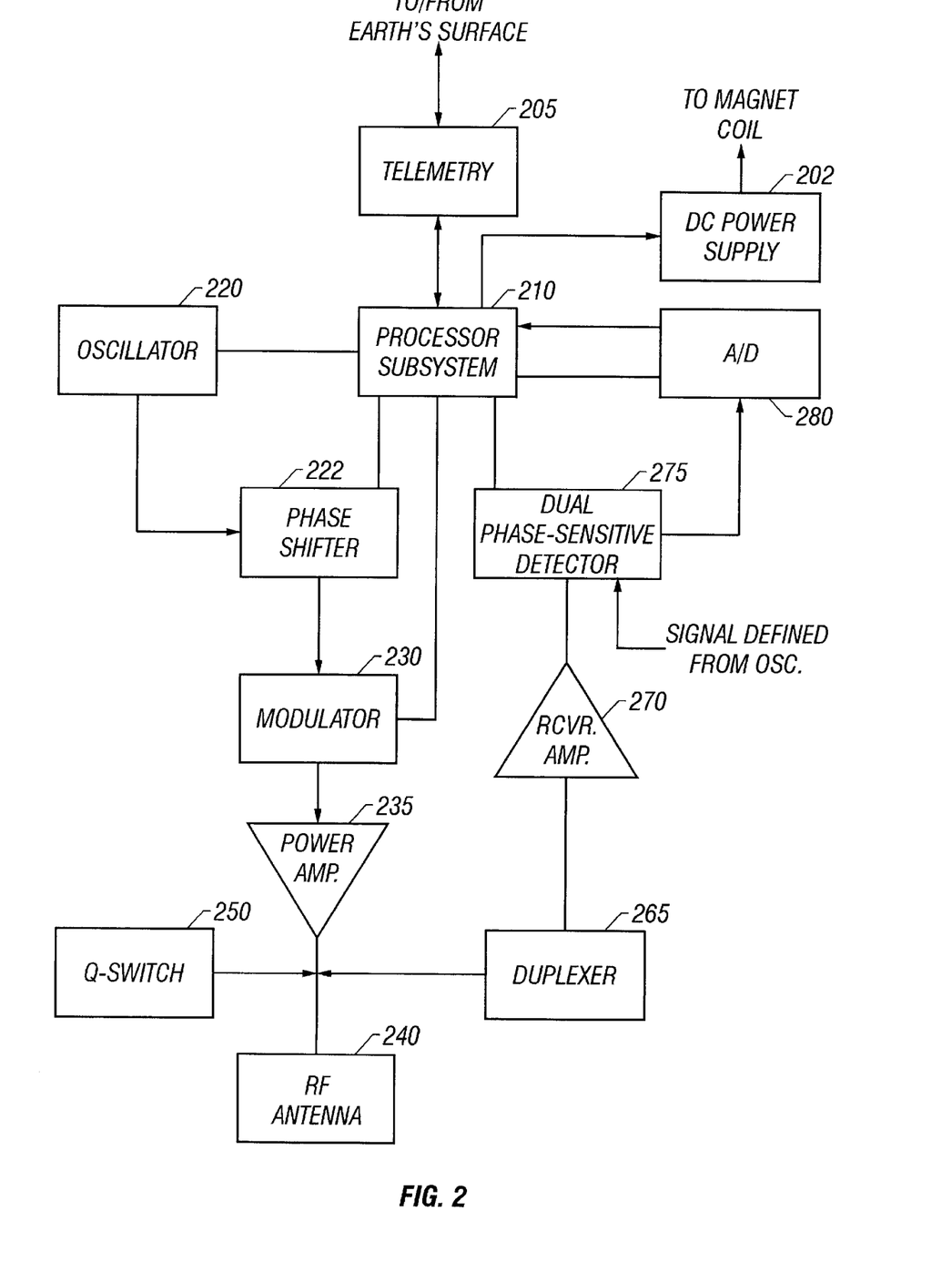
FIG. 2 shows one example of circuitry used in the instrument shown in FIG. 1 for generating an detecting NMR spin echo signals.

Circuitry suitable for making measurements in instruments such as shown in FIG. I is shown in exemplary form in FIG. 2. A processor subsystem 210 disposed in the instrument (30 in FIG. 1) can include thereon memory, timing, interfaces and selected peripheral devices (none shown separately in FIG. 2). The processor subsystem 210 is operatively coupled to a telemetry unit 205 which is adapted to decode command signals from the surface recording system (37 in FIG. 1) and to transmit measurements made by the instrument in a convenient format for decoding and interpretation in the surface recording system (37 in FIG. 1). An oscillator 220 produces alternating current at a selected frequency. The oscillator frequency, as is well known in the art, is typically equal to the nuclear magnetic resonant frequency of the nuclei of interest in the earth formations. Generally, the resonant frequency is related to the amplitude of a static magnetic field induced by a magnet (not shown in FIGS. 1 or 2) and to the gyromagnetic ratio y of the nuclei to be examined by NMR experimentation. The output of the oscillator 220 is coupled, in this example, to a phase shifter 222 and modulator 230, both of which can be operatively controlled by the processor subsystem 210 or by any other means well known in the art to produce alternating current (generally radio frequency—"RF") pulses of desired amplitude and duration. Output of the modulator 230 is coupled to a power amplifier 235 and then to a RF antenna 240 disposed in an appropriate location on the instrument (30 in FIG. 1). Various arrangements for the antenna 240 are well known in the at and are described for example in the previously referred to U.S. Pat. No. 5,055,788 issued to Kleinberg et al, U.S. Pat. No. 5,712,566 issued to Taicher et al and U.S. Pat. No. 4,350,955 issued to Jackson et al. Advantageously, the instrument described in the Kleinberg et al '788 patent includes a Q-switch 250 operatively coupled to the antenna 240 to critically damp the antenna circuit to reduce ringing. The antenna 240 is also coupled, through a duplexer, or switch 265, to a receiver system. The receiver system in this example includes an amplifier 270, a phase sensitive detector 275 (which can receive a phase reference from the oscillator 220), and an analog to digital converter (ADC) 280. Typically the output of the ADC 280 is coupled to the processor subsystem 210 for placing digitized, received NMR signals, among others, in selected channels for transmission to the surface recording system by the telemetry unit 205. It should be understood that including digitized signals in telemetry for transmission to the surface is a matter of discretion for the system designer and is not intended to limit the invention. The processor, for example, could include memory (not shown separately) to store the digitized signals until the instrument (30 in FIG. 1) is removed to the earth's surface.

The processor 210 is also coupled to a control input of a DC power supply 202. Under control of the processor 210, the DC power supply applies a selected voltage, having a selected duration of time, to an electromagnet coil (not shown in FIG. 2). The purpose of the electromagnet coil and the selected DC voltage are to change the amplitude of a static magnetic field induced in the formations of interest (31, 34 in FIG. 1). The manner of changing the static magnetic field amplitude and its purpose in the invention will be further explained.

Figure 3A:
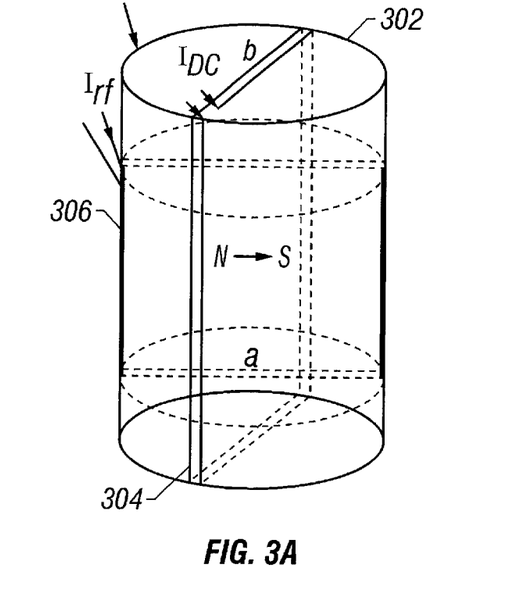
FIGS. 3A and 3B show examples of electromagnet coils used in conjunction with a permanent magnet such as for the apparatus in FIG. 1 to change the static magnetic field amplitude.

Various exemplary embodiments of a primary magnet and the electromagnet coil are shown in FIGS. 3A, 3B, 4, 5A and 5B. FIG. 3A shows an embodiment of the coil 304 which can be used, for example, in an NMR well logging apparatus such as the one shown in U.S. Pat. No. 4,710,713 issued to Taicher et al. The apparatus in the Taicher et al '713 patent includes a permanent magnet (302 in FIG. 3A) that is polarized perpendicularly to the longitudinal axis of the magnet. This magnet induces a DC magnetic field in the earth formation, oriented substantially perpendicularly to a longitudinal axis of the apparatus, and having an amplitude which decreases radially outward from the apparatus. The antenna (equivalent to 240 in FIG. 2) is shown at 306 and is arranged to induce a RF magnetic field which is orthogonal to the static (DC) magnetic field. The magnet coil 304 is arranged to induce a selectable DC magnetic field oriented substantially the same way as the field from the magnet 302. The field from the coil 304 is therefore superimposed on the static field from the magnet 302.

Figure 3B:
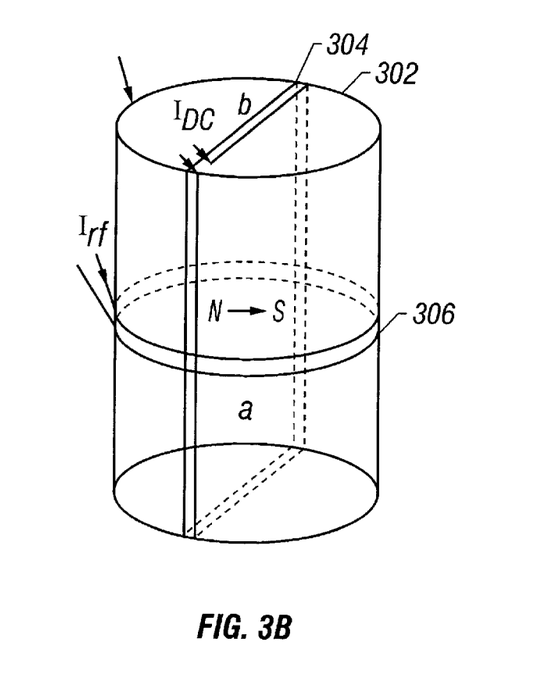

An alternative arrangement of the antenna is shown at 306 in FIG. 3B. The antenna arrangement in FIG. 3B is described, for example, in U.S. Pat. No. 5,712,566 issued to Taicher et al and induces an RF magnetic field generally along the longitudinal axis of the magnet 302.

Figure 4:
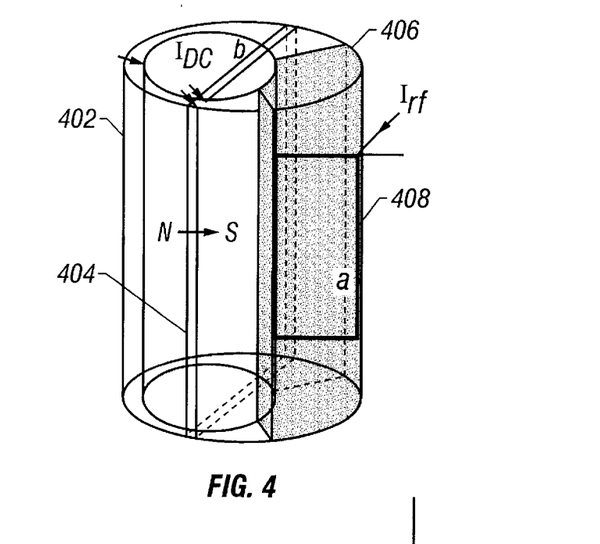
FIG. 4 shows another example arrangement of an electromagnet coil.

FIG. 4 shows an arrangement for the magnet coil 404 which is suitable for use in so-called "pad" type NMR well logging instruments, such as described for example, in U.S. Pat. No. 5,055,788 issued to Kleinberg et al. As is conventional for instruments of the pad type, the magnet 402 is arranged to induce a static magnetic field having selected amplitude distribution generally on one side of the instrument. The antenna 408 is typically disposed on the side of the instrument pressed up against the wall of the wellbore (32 in FIG. 1) to induce the RF magnetic field and detect NMR signals from the earth formations proximate to the one side of the instrument. To improve the efficiency of the antenna 408, a ferrite 406 may be included in the antenna 408 structure. The magnet coil 404 is generally arranged, as in the previous examples, to induce a DC field which is superimposed on the static field in a zone of investigation (referred to as sensitive volume) in which NMR is excited and detected.

Figure 5A:
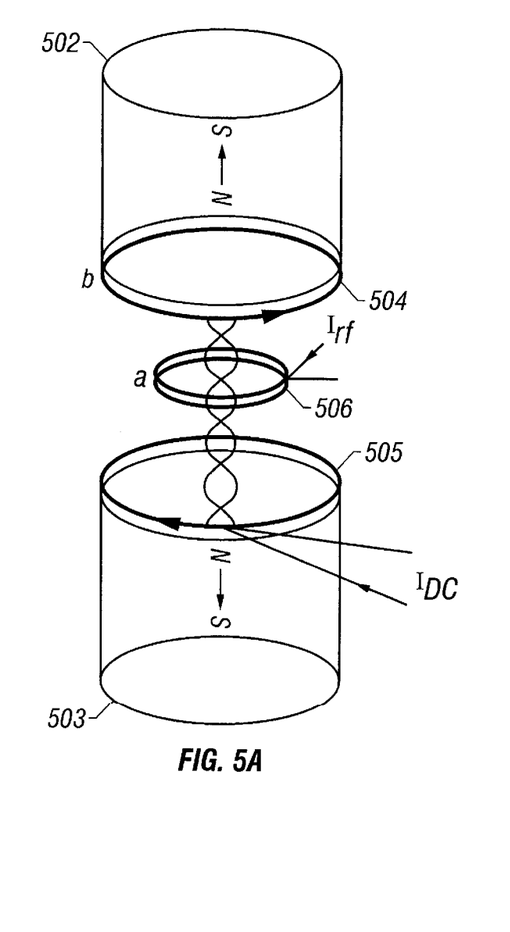
FIGS. 5A and 5B show two other examples of electromagnet coil arrangements.
Figure 5B:
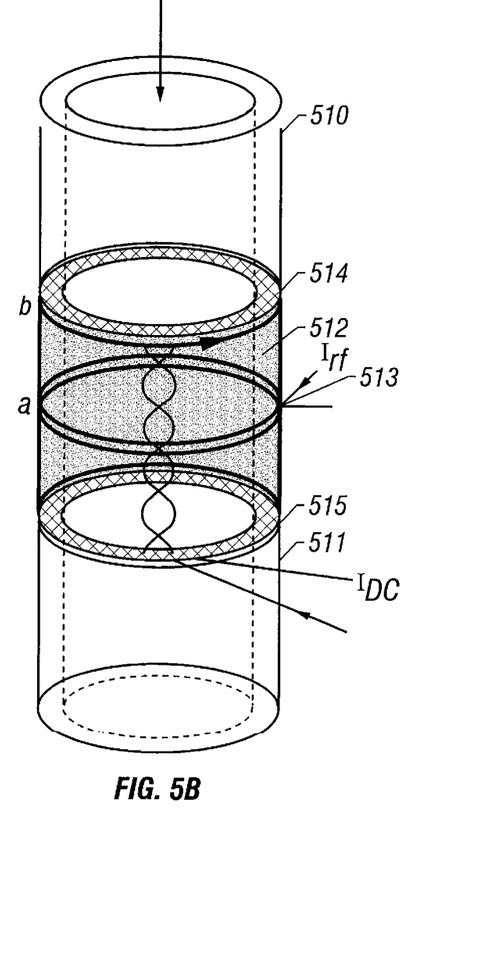

Yet another arrangement of the electromagnet coil is shown at 504 and 505 in FIG. 5A. The arrangement of magnets 502, 503 and the antenna 506 in FIG. 5A is similar to than of an apparatus described in U.S. Pat. No. 4,350,955 issued to Jackson et al. An example adaptation of the apparatus shown in the Jackson et al '955 patent, suitable for use in measurement-while-drilling (MWD) systems is shown in FIG. 5B. The adaptation shown in FIG. 5B includes permanent magnets oriented as shown at 510 and 511, magnet coils shown a 514 and 515, and an antenna coil shown at 513. The adaptation shown in FIG. 5B may include a ferrite 512 to improve the efficiency of the antenna 513 and/or magnet coils 512, 515. The coils in the examples shown in FIGS. 5A and 5B, just as in the previous examples, is arranged to induce a selected amplitude and duration DC magnetic field superimposed on the static magnetic field induced by the magnets within the sensitive volume.

While the various examples of primary magnet and electromagnet coil structures shown herein include a permanent magnet and an appropriately arranged electromagnet to provide a selectable amplitude static magnetic field in the sensitive volume, it should be clearly understood that any suitable arrangement of permanent and/or electromagnets can be used to accomplish the same result. For example, an electromagnet can both provide the principal static magnetic field, and can be coupled to a suitably controllable DC power supply so as to be able to induce a static magnetic field whose amplitude can be controlled according to the description which follows. Accordingly, the structures shown in the examples of FIGS. 3A, 3B, 4, 5A and 5B are not meant to limit the scope of this invention.

Having shown various examples of structures by which a selected amplitude and duration DC magnetic field can be superimposed on the static magnetic field of typical NMR well logging instruments, the nature of the superimposed DC field and its purpose will now be explained.

As in the previous examples, when a voltage of selected amplitude is applied to the electromagnet coil (408 in FIG. 4) the DC field it induces is superimposed on the static magnetic field induced by the magnet. Alternatively, where an electromagnet is used in place of a permanent magnet for inducing the primary static magnetic field, the total magnitude of the static magnetic field can be selected to vary according to the scheme which will be further explained herein. However implemented, this has the effect of changing the static magnetic field amplitude within the sensitive volume. When the amplitude of the static magnetic field is changed, the nuclear magnetic resonant (Larmor) frequency of excited nuclei in the sensitive volume changes correspondingly. In this embodiment of the invention, the static magnetic field amplitude $B_0$ is adjusted by an amount $\Delta B_0$ during a period of time between the end of a first nuclear spin reorienting pulse (90 degree pulse) and the beginning of a spin-refocusing pulse (180 degree pulse) forming parts of a standard Carr-Purcell-Meiboom-Gill (CPMG) spin-echo NMR measurement sequence.

When the static field amplitude is changed, the Larmor frequency changes by an amount $\Delta\omega$ corresponding to $\Delta B_0$. This is shown in the following expression:

$$\Delta\omega = \gamma \Delta B_0 \qquad (1)$$

Because the 90 degree reorienting pulse has ended at the time the static magnetic field amplitude is changed, or adjusted, ringing induced in the antenna structure by the 90 degree RF pulse will oscillate at the selected RF frequency. Precession of the nuclear magnetic spins, and their resonant frequency, change during the time the static field amplitude is adjusted. The nuclear magnetic spins will return to the original resonant frequency after the adjustment to the static field amplitude ends (which in this embodiment is before the application of the first 180 degree pulse). A phase change between ringing and echo signals will result as a result of the change in resonant frequency. This phase change is used in the invention to enable signal combination to substantially cancel ringing.

The total signal, denoted by S(t), detected by the logging instrument (30 in FIG. 1) includes baseline, dc, random noise, $S_{noise}$, ringing induced both by the 90 degree and 180 degree pulses, $R_{90}$ and $R_{180}$, respectively, and spin echo components, $S_{echo}$. The total signal can be described by the following expression:

$$S(t) = S_{echo}\exp(-i\omega_0 t) + R_{90}\exp(-i\omega_R t) + \qquad (2)$$
$$\sum_n R_{180}\exp(-i\omega_R(t-nT_E)) + S_{noise} + dc$$

where $T_E$ represents the interecho spacing time (time between successive 180 degree RF refocusing pulses) and $\omega_R$ represents the ringing frequency. Where the static magnetic field amplitude has been adjusted by the amount $\Delta B_0$ during the selected time period, beginning at $t_1$ and ending at $t_2$, the expression for the total signal becomes:

$$S(t, \Delta B_0) = S_{echo}\exp(-i(\omega_0 t + \Delta\omega(t_2 - t_1))) + \qquad (3)$$
$$R_{90}\exp(-i\omega_R t) + \sum_n R_{180}\exp(-i\omega_R(t-nT_E)) + S_{noise} + dc$$

In this example, the spin echo signals undergo the phase shift, denoted by $\phi$, which can be determined by the expression:

$$\phi = \Delta\omega(t_2 - t_1) = \gamma \Delta B_0(t_2 - t_1) \qquad (4)$$

The phase shift, as shown in equation (4) depends on the magnitude of adjustment to the static magnetic field amplitude and on the duration of the adjustment (length of the selected time period). In this embodiment, the phase shift $\phi$ applied to the one CPMG sequence should be selected to be 180 degrees, or any odd-numbered multiple of 180 degrees (e.g. 540 degrees or 900 degrees), but not 360 degrees or any even-numbered multiple of 180 degrees. The phase shift can be selected by appropriate selection of time difference $(t_2-t_1)$ and/or magnitude of the static field amplitude adjustment $\Delta B_0$. As a practical matter, the time difference will be limited to a maximum value of about 100 microseconds because the minimum time between 90 degree and 180 degree pulses is about 100 microseconds for typical NMR well logging instruments.

In this particular embodiment of the invention, two CPMG spin echo sequences are measured. One sequence includes the adjustment to the static magnetic field amplitude. The other CPMG sequence excludes the static magnetic field amplitude adjustment. The measurements in one of these sequences is then time correspondingly subtracted from the measurements in the other sequence to generate a signal in which any baseline bias, and both 90 degree and 180 degree RF pulse-induced ringing have been canceled. An expression for such a difference signal is:

$$S(t) - S(t, \Delta B_0) = 2S_{echo}\exp(-iw_0 t) \qquad (5)$$

Although the embodiment described herein includes two complete CPMG sequences, it should be understood that the embodiment fairly contemplates any number of spin echoes in each sequence, including only one spin echo.

The second one of the CPMG sequences in this embodiment will typically be performed after a suitable wait time during which the nuclear magnetic spins of the excited nuclei can become substantially aligned with the static magnetic field. The duration of the wait time is generally related to the longitudinal relaxation time ($T_1$) of the nuclei being excited.

As a practical matter, the phase reference for the phase sensitive detector (275 in FIG. 2) will have to be adjusted so that the signal detection will be phase-aligned with the phase-shifted spin echoes in the one of the sequences have the phase-shifted spin echoes. Means for selecting a suitable phase reference are well known in the art.

Figure 6A:
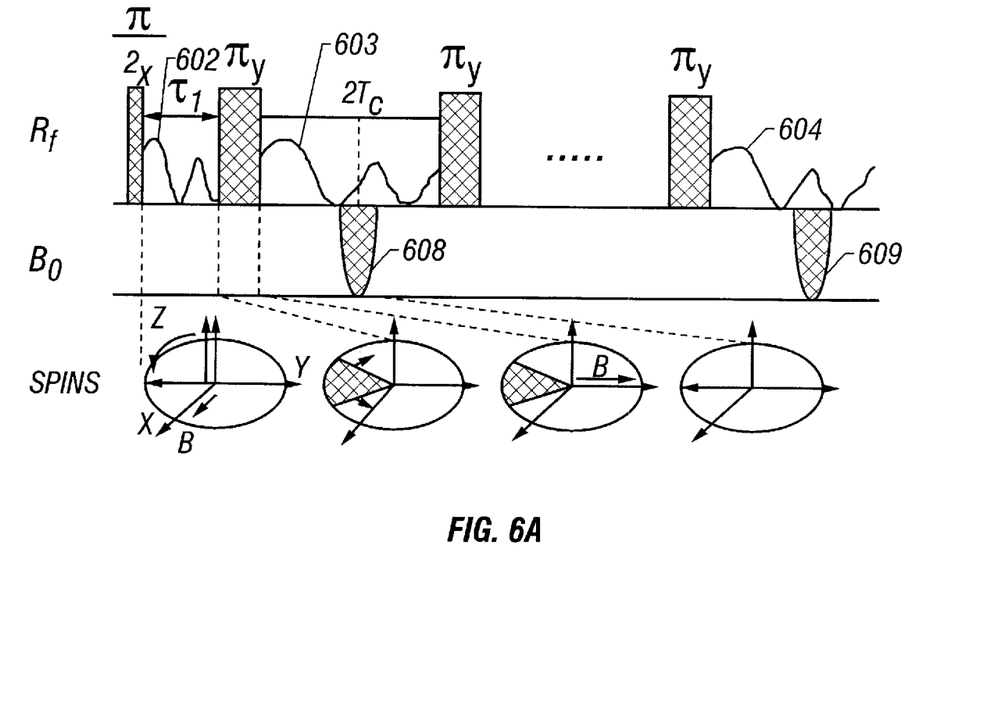
FIGS. 6A and 6B show a pulse timing diagram and nuclear spin diagram for an example of one embodiment of the invention.
Figure 6B:
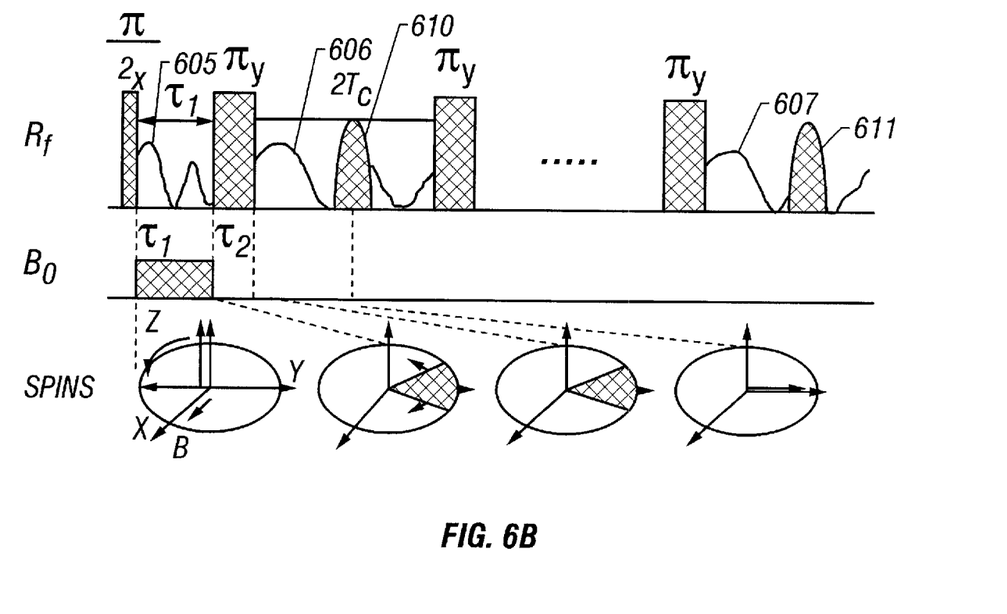

Timing diagrams, and corresponding nuclear spin axis polarization diagrams for this example embodiment are shown in FIGS. 6A and 6B. FIG. 6A shows pulses and spins for part of a conventional CPMG sequence, including a 90 degree pulse (indicated as $\pi/2$ in FIG. 6A) to reorient the spin axes of nuclei in the sensitive volume perpendicular to the static magnetic field, and a succession of 180 degree pulses (indicated by $\pi$ in FIG. 6A) to refocus the nuclear magnetization, each such 180 degree pulse generated after a selected interecho spacing time $2T_c$. Ringing and noise during spin-echo detection times is shown generally at 602, 603 and 604. Induced spin echoes are shown as having negative polarity along the y-axis, generally at 608 and 609 in FIG. 6A. FIG. 6B shows a CPMG pulse sequence as in FIG. 6A, but in this pulse sequence, the static field amplitude $B_0$ is adjusted, as previously explained, by an amplitude and time span, shown between $t_1$ and $t_2$, selected to cause a 180 degree phase shift in the spin echo signals, shown generally at 610 and 611 Baseline noise and ringing shown at 605, 606 and 607 in FIG. 6B will substantially cancel when the signals shown in FIG. 6A are subtracted from the signals shown in FIG. 6B (or the reverse).

For hydrogen nuclei, and a time span of 100 microseconds, the amount of adjustment needed to provide a phase shift in the spin echoes of 180 degrees is 1.1743 Gauss. This amount of static magnetic field adjustment is easily developed using conventional electromagnets arranged as in the various embodiments shown previously.

An alternative embodiment of the invention includes adjustment of the static magnetic field amplitude by a selected amount $\Delta B_0$ for a selected time interval between the 90 degree reorienting pulse and a first 180 degree refocusing pulse of a sequence of such refocusing pulses. Spin echo amplitudes are measured between each one of the refocusing pulses as is conventional for such measurements. In this embodiment, the RF magnetic field for the refocusing pulses is applied along the x-axis direction, as contrasted with the first embodiment wherein the 180 degree refocusing pulses are applied along the y-axis direction. After the sequence of measurements is completed, and after a suitable wait time, the measurement sequence is repeated, this time applying an adjustment in amplitude to the static magnetic field during the same relative time span, but having opposite polarity ($-\Delta B_0$) to the adjustment applied during the previous measurement sequence. In this embodiment, the two adjustments to the static magnetic field have amplitude and duration adapted to provide the same magnitude phase shift to the corresponding sets of spin echoes, but of opposite polarity. One of the two sequences is then time, correspondingly subtracted from the other sequence to provide a measurement in which the baseline and ringing are substantially canceled. Expressions for the signals measured in each sequence are:

$$S(t, \Delta B_0) = S_{echo} \exp(-i\omega_0 t + \varphi) + \qquad (6)$$
$$R_{90}\exp(-i\omega_R t) + \sum_n R_{180}\exp(-i\omega_R(t - nT_E)) + S_{noise} + dc$$

$$S(t, \Delta B_0) = S_{echo} \exp(-i(\omega_0 t - \varphi) + R_{90}\exp(-i\omega_R t) + \qquad (7)$$
$$\sum_n R_{180}\exp(-i\omega_R(t - nT_E)) + S_{noise} + dc$$

The phase shift in this embodiment is selected (by appropriate selection of adjustment amplitude and time span) to be an odd-numbered multiple of 90 degrees. In this case, the time correspondent difference between the signals measured within the two pulse sequences can be determined by the following expression:

$$S(t, -\Delta B_0) - S(t, -\Delta B_0) = 2S_{echo}\exp(-\omega_0 t) \qquad (8)$$

The absolute value of the amplitude of adjustment to the static magnetic field amplitude in this embodiment is about half the amount required in the previous embodiment. For a time span ($t_2-t_1$) of 100 microseconds, and for hydrogen nuclei, the amplitude of the adjustment to the static magnetic field is about 0.5872 gauss in this embodiment.

Figure 7A:
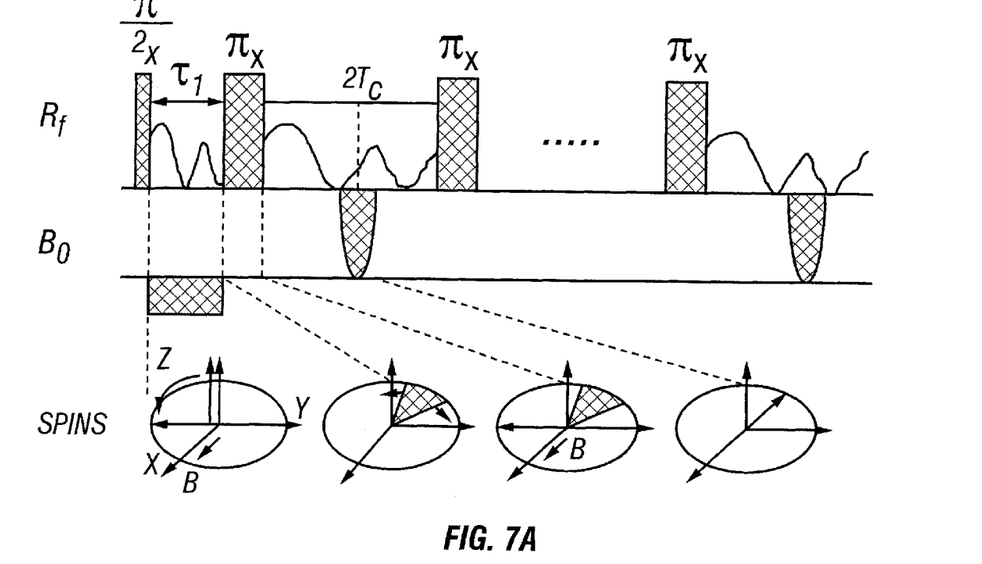
FIGS. 7A and 7B show a pulse timing diagram and nuclear spin diagram for an example of another embodiment of the invention.
Figure 7B:
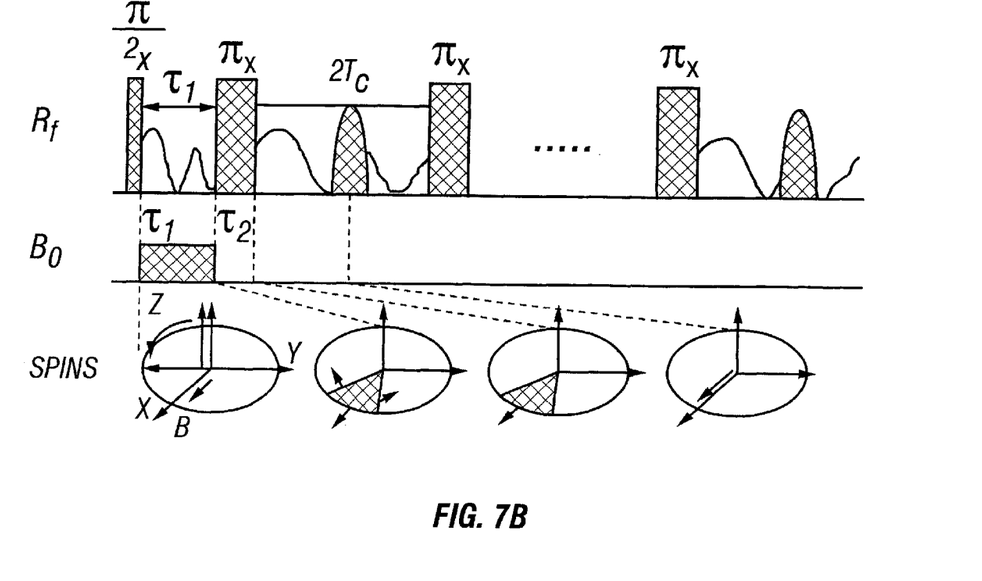

Timing diagrams and spin polarization charts for this embodiment are shown in FIGS. 7A and 7B. FIG. 7A shows a pulse sequence including an adjustment to the static magnetic field amplitude of $-\Delta B_0$ being applied between the 90 degree pulse and the first 180 degree pulse of the measurement sequence. In FIG. 7B, the opposite polarity adjustment to the static field amplitude, $\Delta B_0$ is shown as being applied between the 90 degree pulse and the first 180 degree pulse.

It should be noted that although both embodiments described herein show the adjustment to the static magnetic field amplitude being applied between the 90 degree polarization pulse and the first 180 degree refocusing pulse, the invention will work for any other timing of the adjustment to the static magnetic field amplitude, provided that such adjustments do not occur when any one of the RF pulses are being transmitted. Changing the static magnetic field amplitude during transmission of a RF pulse will change the frequency of the ringing.

It should be apparent from the description of the second embodiment and the equations describing the total signals therein for each of the two sequences of spin echo measurements that the invention can be more broadly described as performing a first spin echo NMR measurement, to which a first selected phase shift is applied to the first spin echo measurement, and then performing a second NMR spin echo measurement to which a second selected phase shift is applied to the second spin echo measurement. A difference is calculated between the two spin echo measurements. The difference represents the spin echo amplitude wherein ringing and baseline have been substantially canceled. The first and second selected phase shifts must sum to an odd numbered multiple of 180 degrees. Some embodiments of the invention includes making a sequence of spin echo measurements corresponding to each of the two selected phase shifts. In these embodiments, a time correspondent difference is determined between the two sequences to calculate a sequence in which the ringing and baseline have been substantially canceled.

The various embodiments of the invention described herein can also be used with well logging apparatus forming part of a drilling tool string. Well logging apparatus forming part of a drilling tool string are generally adapted to make measurements of formation properties by moving the drilling tool string along the wellbore. Moving the drilling tool string generally takes place during the drilling of a wellbore by a drill bit, but also includes "pipe trips" where the drilling tool string is partially or totally removed from the wellbore. Such well logging instruments are known in the art as measurement while drilling (MWD) or logging while drilling (LWD) instruments. Several MWD instruments are known in the art which make nuclear magnetic resonance measurements, any of which can be adapted to use the present invention. Such MWD instruments are described, for example, in U.S. Pat. No. 5,757,186 issued to Taicher et al, U.S. Pat. No. 5,280,243 issued to Miller and published European patent application no. 0 581 666 filed by Kleinberg and assigned to the assignee of the present invention.

The foregoing invention has been described with respect to example embodiments, but it should be apparent to those skilled in the art that other embodiments of this invention can be devised which do not depart from the spirit of the invention as disclosed herein. Accordingly, the invention shall be limited in scope only by the attached claims.

What is claimed is:

1. A method for reducing ringing in nuclear magnetic resonance measurements, comprising:
   inducing a static magnetic field in a sensitive volume to orient nuclear magnetization of nuclei therein;
   reorienting said nuclear magnetization by a first selected angle;
   adjusting an amplitude of said static magnetic field to cause a first selected phase shift in a spin echo signal measured subsequently;
   reorienting said nuclear magnetization by a second selected angle;
   detecting a first spin echo signal;
   repeating said reorienting by said first selected angle after a selected wait time;
   repeating said adjusting said amplitude of said static magnetic field to cause a second selected phase shift in a subsequently measured spin echo, said first and said second selected phase shifts having a difference therebetween of an odd numbered multiple of 180 degrees;
   repeating said reorienting by said second selected angle;
   detecting a second spin echo signal; and
   determining a difference between said first spin echo signal and said second spin echo signal.

2. The method as defined in claim 1 wherein said reorienting comprises applying an oscillating magnetic field to said sensitive volume, said oscillating magnetic field having an amplitude and duration selected to cause reorientation by a selected angle, said first selected angle is 90 degrees and said second selected angle is 180 degrees.

3. The method as defined in claim 1 wherein said first selected phase shift is zero and said second selected phase shift is 180 degrees.

4. The method as defined in claim 1 wherein said first selected phase shift is 90 degrees and said second selected phase shift is −90 degrees.

5. The method as defined in claim 1 further comprising:
   repeating said reorienting by said second selected angle and measuring a plurality of said first spin echoes prior to said wait time;
   repeating said reorienting by said second angle and measuring a plurality of said second spin echoes after said wait time; and
   calculating a time correspondent difference between said first spin echoes and said second spin echoes.

6. The method as defined in claim 5 further comprising determining a rate of decay of spin echo amplitude from said difference.

7. The method as defined in claim 5 wherein said adjusting of said static magnetic field amplitude is performed between any two occurrences of said reorienting by said second selected angle.

8. The method as defined in claim 1 wherein said adjusting comprises applying a selected voltage to an electromagnet coil.

9. The method as defined in claim 1 wherein said reorienting said nuclear magnetization by said first and said second selected angle comprises inducing a radio frequency magnetic field in said sensitive volume, said radio frequency magnetic field having a first amplitude and duration selected to cause said reorientation by said first selected angle, said radio frequency magnetic field having a second amplitude and duration selected to cause said reorientation by said second selected angle, said radio frequency magnetic field substantially orthogonal to said static magnetic field in said sensitive volume.

10. A method for evaluating nuclear magnetic resonance properties of earth formations penetrated by a wellbore, comprising:

inserting a well logging instrument into a wellbore, said instrument comprising a magnet for inducing a static magnetic field in said formations, at least one antenna for transmitting signals into and receiving signals from said formations, said instrument comprising circuitry adapted to transmit oscillating current through said at least one antenna and to detect voltages induced in said antenna;

inducing a static magnetic field in a sensitive volume disposed in said earth formations to orient nuclear magnetization of nuclei therein;

reorienting said nuclear magnetization by a first selected angle;

adjusting an amplitude of said static magnetic field to cause a first selected phase shift in a spin echo signal measured subsequently;

reorienting said nuclear magnetization by a second selected angle;

detecting a first spin echo signal;

repeating said reorienting by said first selected angle after a selected wait time;

repeating said adjusting said amplitude of said static magnetic field to cause a second selected phase: shift in a subsequently measured spin echo, said first and said second selected phase shifts having a difference therebetween of an odd numbered multiple of 180 degrees;

repeating said reorienting by said second selected angle;

detecting a second spin echo signal; and determining a difference between said first spin echo signal and said second spin echo signal, said difference corresponding to spin echo amplitude in said earth formations.

11. The method as defined in claim 10 wherein said reorienting comprises applying an oscillating magnetic field to said sensitive volume, said oscillating magnetic field having an amplitude and duration selected to cause reorientation by a selected angle, said first selected angle is 90 degrees and said second selected angle is 180 degrees.

12. The method as defined in claim 10 wherein said first selected phase shift is zero and said second selected phase shift is 180 degrees.

13. The method as defined in claim 10 wherein said first selected phase shift is 90 degrees and said second selected phase shift is −90 degrees.

14. The method as defined in claim 10 further comprising:

repeating said reorienting by said second selected angle and measuring a plurality of said first spin echoes prior to said wait time;

repeating said reorienting by said second angle and measuring a plurality of said second spin echoes after said wait time; and     calculating a time correspondent difference between said first spin echoes and said second spin echoes.

15. The method as defined in claim 14 further comprising determining a rate of decay of spin echo amplitude from said difference.

16. The method as defined in claim 14 wherein said adjusting of said static magnetic field amplitude is performed between any two occurrences of said reorienting by said second selected angle.

17. The method as defined in claim 10 wherein said adjusting comprises applying a selected voltage to an electromagnet coil.

18. The method as defined in claim 10 wherein said reorienting said magnetization by said first and said second selected angle comprises inducing a radio frequency magnetic field in said sensitive volume, said radio frequency magnetic field having a first amplitude and duration selected to cause said reorientation by said first selected angle, said radio frequency magnetic field having a second amplitude and duration selected to cause said reorientation by said second selected angle, said radio frequency magnetic field substantially orthogonal to said static magnetic field in said sensitive volume.

19. The method as defined in claim 10 further comprising:

moving said instrument a selected distance along said wellbore;

repeating all of said method from said inducing to said determining said difference for a selected interval along said wellbore; and     repeating said moving and said repeating all of said method until a selected interval of said wellbore has been traversed.

20. The method as defined in claim 19 wherein the instrument forms part of a drilling tool string, and the moving the instrument is performed by moving the drilling tool string along the wellbore.

\* \* \* \* \*